United States Patent [19]

Maltby, Jr.

[11] Patent Number: 4,837,449

[45] Date of Patent: Jun. 6, 1989

[54] INSPECTING FOR MATCHING OF PAIRED SHEETS OF TRANSPARENT MATERIAL

[76] Inventor: Robert E. Maltby, Jr., 7869 McCutcheonville Rd., Wayne, Ohio 43466

[21] Appl. No.: 193,574

[22] Filed: May 16, 1988

[51] Int. Cl.$^4$ .................................... G01N 21/86
[52] U.S. Cl. ........................ 250/571; 356/239
[58] Field of Search ............... 250/560, 563, 572, 571; 356/371, 382, 239

[56] References Cited

U.S. PATENT DOCUMENTS

| | | | |
|---|---|---|---|
| 1,756,785 | 4/1930 | Gallasch | 356/382 |
| 2,379,263 | 6/1945 | Vine | 356/371 |
| 3,307,446 | 3/1967 | Rottmann | 356/382 |
| 3,807,870 | 4/1974 | Kalman | 356/239 |
| 3,919,531 | 11/1975 | Bobel, II et al. | 250/563 |
| 4,249,823 | 2/1981 | Task | 356/239 |
| 4,289,400 | 9/1981 | Kubota et al. | 356/371 |
| 4,377,341 | 3/1983 | Task et al. | 356/371 |

*Primary Examiner*—David C. Nelms
*Assistant Examiner*—Michael Messinger
*Attorney, Agent, or Firm*—Richard C. Darr

[57] ABSTRACT

Inspecting paired sheets of transparent material for determining their fit or conformity to one another. A highly collimated light beam, such as a laser beam, is directed through a pair of transparent sheets supported in closely spaced or nested relationship. The major surfaces of each sheet are known to be substantially parallel. As the primary beam passes through the sheets, beams are reflected from each of the four surfaces. The reflected beams are re-reflected from the next surface encountered to pass beyond the pair of sheets. Beams reflected from the parallel front and rear surfaces of each sheet exit the sheets parallel to and closely spaced from the primary transmitted beam. If the adjacent interior or second and third surfaces of the pair of sheets are not parallel at the point of inspection, as where the two sheets do not properly nest or conform, the beam reflected from the third surface and re-reflected from the second surface is deflected relative to the primary beam. The beams are intercepted upon emerging from the sheets. The displacement of the reflected beam from the transmitted beam indicates the angular relationship between the sheets at the point of inspection.

22 Claims, 2 Drawing Sheets

INSPECTING FOR MATCHING OF PAIRED SHEETS OF TRANSPARENT MATERIAL

BACKGROUND OF THE INVENTION

1. Field of the Invention

This invention pertains generally to inspecting sheets of transparent material, and more particularly to observing paired sheets of glass or other transparent material for determining the angular relationship or degree of fit or match of the sheets.

2. Description of the Prior Art

In the flat glass field there are many instances where it is highly desirable to determine whether a sheet of glass has a particular predetermined surface configuration or, more specifically, in what areas and to what degree the sheet deviates from a desired configuration. Such information is of particular significance in the automotive glazing field where glass sheets are bent to various curved forms for utilization as side lites, rear windows, roof panels and windshields. In order to fit properly and meet automotive manufacturers rigid quality standards, as well as government-imposed standards for optical clarity, it is necessary that individually fabricated units conform within narrow limits to a standard configuration. This is particularly true in the fabrication of laminated glazing units wherein matching sheets of glass are laminated under heat and pressure to a plastic interlayer member. Such sheets are formed by pressing heat-softened sheets individually into conformity with a mold or by gravity bending sheets in pairs in order to insure that their configurations closely match. Despite the best-efforts through years of experience in bending glass for such units, it is found that some of the bent sheets warp or distort upon subsequent cooling. This is particularly true in the case of present day laminated windshields in which one of the sheets of the pair may have an opaque band painted on the surface around the edge to conceal the means by which the unit is mounted in the vehicle. The band seems to cause uneven cooling and subsequent warping of the sheet. As a result, when paired the bent sheets will have areas that do not conform to one another. In other words, when the sheets are nested one upon the other, there will be gaps between the two sheets in certain areas. This lack of conformity is not visually detectable. When such sheets are subsequently laminated under heat and pressure to the thin plastic interlayer, they bend into conformity, that is, they assume corresponding configurations. However, in doing so undesirable stresses are created in the sheets. The stresses or residual forces may tend to cause delamination or separation of the sheets from the interlayer over a period of time. More importantly, on forcing the sheets into conformity with one another during laminating, some portions of the outer surfaces of the sheets are placed in tension. As is well known, glass has great strength in compression, but does not function well in tension. The outboard surfaces of laminated vehicle windshields are often subjected to impact by flying objects such as stones and gravel thrown up from the road surface by other vehicles. Where the glass surface is not under stress, such impinging objects may merely scratch or pit the surface of the glass, and the windshield will not be severely damaged. However, if the glass is under tension at the point of impact, cracks or stress fractures may radiate from the damaged area, rendering the windshield unfit for further use. Replacement of the windshield is inconvenient and expensive, and the cracked windshields have resulted in numerous complaints from vehicle owners.

The flat or curved tempered glass parts utilized for present day automobile side and rear window glazings must conform to a predetermined configuration in order to properly fit into the opening provided therefore in the vehicle body. As is well known, such glass parts may warp during the heating and subsequent chilling utilized in their fabrication, resulting in randomly produced parts having a configuration falling outside acceptable tolerances. Heretofore, detection of such units was time consuming and unreliable, often resulting in defective units reaching the automobile assembly line before they were discovered.

Determination of the planar alignment of two sheets of glass relative to one another is important in certain glass fabricating operations. Thus, in the production of multiple sheet insulating glass units the spaced sheets of glass must be parallel to minimize distortion of objects viewed through the finished unit. The invention is particularly adapted to determining such parallelism during production and as a means of checking the finished units for compliance with quality standards.

SUMMARY OF THE INVENTION

In accordance with the present invention, there is provided a method and apparatus for inspecting for shape or configuration any flat or curved transparent material. Thus, paired pieces of glass such as those to be laminated for producing an automotive vehicle windshield can be inspected to determine their fit or conformity one to the other. Likewise, spaced sheets of transparent material can be checked for parallelism, and individual sheets of transparent material can be inspected for conformance to a desired configuration. A highly collimated light beam, preferably a laser beam, is directed through a pair of transparent sheets supported in closely spaced or nested relationship. The opposite major surfaces of each sheet are known to be essentially parallel. As the beam passes through the transparent sheets, secondary beams will be reflected from each of the glass surfaces. These reflected beams are then re-reflected from the next glass surface encountered to pass beyond the pair of sheets. Since the opposite surfaces of each sheet are essetially parallel, the beams reflected between the surfaces of each sheet exit the glass essentially parallel to and closely spaced from the primary transmitted beam. The adjacent interior surfaces of the pair of sheets, that is, the second and third surfaces, will only be parallel if the sheets themselves are parallel at that point. If the sheets are not parallel at that point, as where the two sheets do not nest properly, the beam reflected from the third surface and re-reflected from the second surface, is deflected relative to the primary transmitted beam by an angle twice that between the second and third surfaces as it exits the glass. The transmitted and reflected beams are intercepted after exiting the glass pair, and the displacement of the reflected beam from the transmitted beam is analyzed to indicate the angular relationship between the sheets at the point of inspection. The direction in which the reflected beam is displaced from the transmitted beam indicates the direction in which the two sheets are off parallel, while the distance between the beams indicates the magnitude of non-parallelism.

It is, therefore, a primary object of the invention to provide a method and apparatus for inspecting for shape a flat or curved sheet of transparent material.

Another object of the invention is to provide a method and apparatus for inspecting paired pieces of transparent material for fit or nesting to one another.

Another object of the invention is to provide a method and apparatus for determining the angular relationship between spaced sheets of transparent material.

Still another object is to provide a method and apparatus for determining conformity of the shape of a transparent sheet to that of a standard transparent sheet having the desired shape.

Other objects and advantages will become more apparent during the course of the following description when taken in connection with the accompanying drawings.

BRIEF DESCRIPTION OF THE DRAWINGS

In the drawings, wherein like numerals refer to like parts throughout.

DESCRIPTION OF THE PREFERRED EMBODIMENTS

Figure 1:
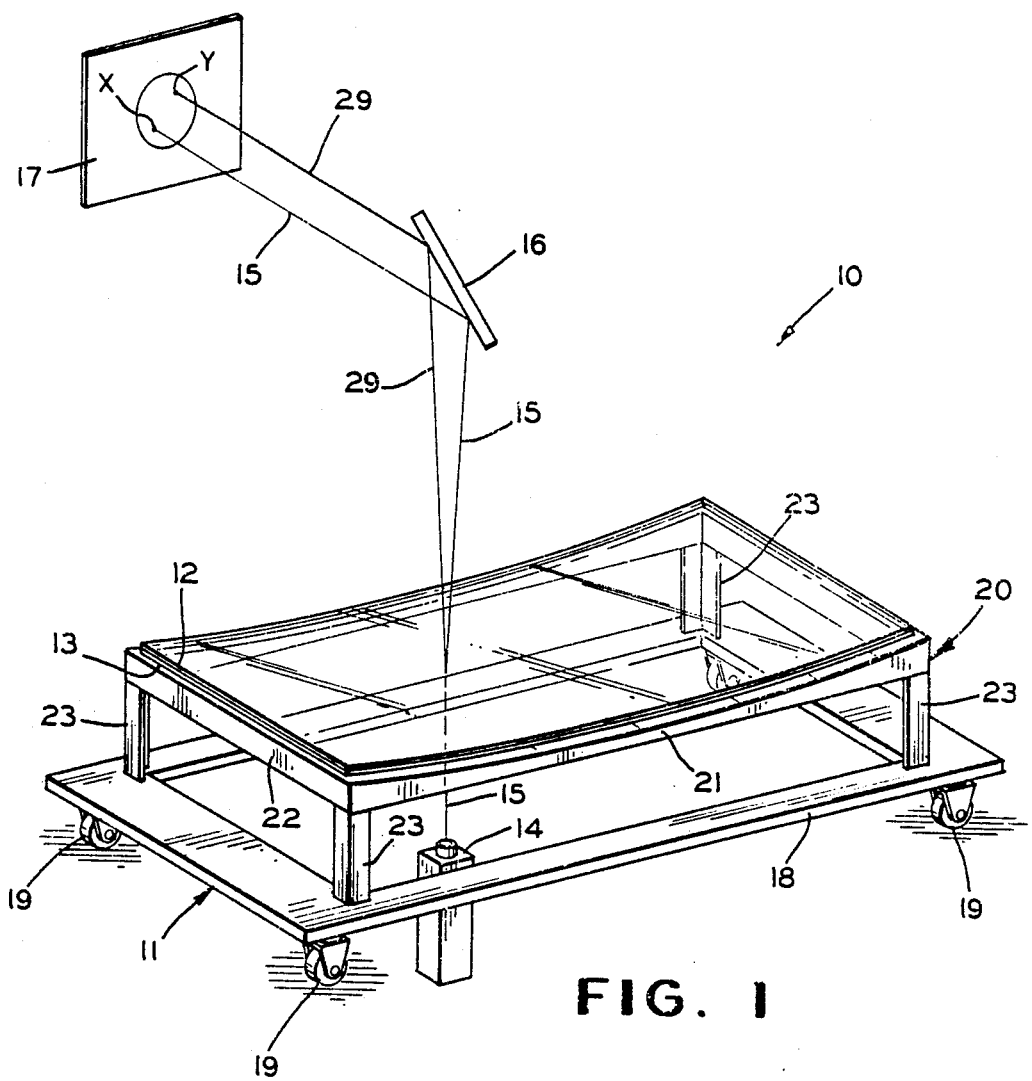
FIG. 1 is a schematic perspective view of a system for practicing the invention.

Referring now to the drawings, there is illustrated schematically at 10 in FIG. 1 a system which may be employed in inspecting transparent sheets in accordance with the invention. More particularly, the system is adapted for inspecting superimposed pairs of sheets for matching with one another and comprises a mobile base 11 upon which are carried a pair of upper and lower transparent sheets 12 and 13, respectively. As will be hereinafter explained, depending upon the purpose for which they are being examined, the upper sheet 12 may be nested directly upon the lower sheet 13 or it may be supported closely spaced thereabove. Positioned beneath the mobile base is a light source 14 for emitting a highly collimated beam 15 upwardly through the sheets 12 and 13. The beam is preferably directed nearly normal to the surface of the sheet 13. However, the invention will function as well if the beam is within a few degrees of normal to the surface, thereby enading curved sheets to be inspected over their entire area without changing the direction of the light sources. The light source 14 may advantageously be a helium-neon laser unit. A mirror 16 located above the mobile base 11 is positioned to receive the light beams from the sheets and direct them to a stationary target 17. The target preferably has a white or other light colored surface so that the points at which the light beams strike it will be readily visible.

The mobile base 11 supports the sheets 12 and 13 so that they can be moved relative to the light source 14 for observing different areas of the sheets. To that end, the mobile base may comprise a peripheral frame 18 having caster wheels 19 at its corners. A stand 20 resting upon the base includes narrow side members 21 interconnected by end members 22 and supported by legs 23. The frame 18 and stand 20 are so constructed as to support the glass sheets along a narrow band around their periphery, on the order of ½ to ¾ inch in width, while leaving the central area open and unobstructed so that the mobile base can be manually moved around to direct the beam 15 through selected areas of the sheets. Of course, it is fully contemplated that the invention might also be practiced by maintaining the glass sheets stationary and moving the light source, mirror and target as a unit to observe the different areas. Likewise, it will be understood the mobile base may comprise part of a conveyor or carrier system as in a fabricating line or the like. Also, it will be understood that the stand 20 may be modified to support the sheets 12 and 13 in closely spaced relationship where desired for a particular inspection procedure. For example, a spacer member (not shown) may be provided between the sheets around their periphery.

Figure 2:
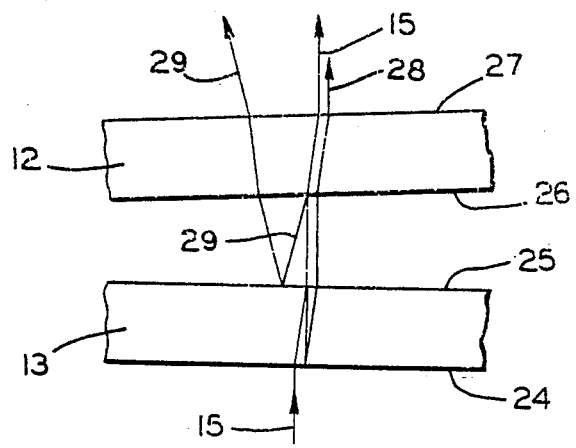
FIG. 2 is an enlarged schematic view illustrating the paths followed by the beams in passing through the transparent sheets.

There is illustrated in FIG. 2 the manner in which the beams of the invention travel within and through the sheets. It is assumed the sheets 12 and 13 will have parallel or nearly parallel surfaces as is the case with so-called float glass, from which most present day automotive glazing units are fabricated. The sheets thus may be said to have first, second, third and fourth surfaces in the sequence in which the beam passes, identified at 24, 25, 26 and 27, respectively. The surfaces 24 and 25 will be parallel as will the surfaces 26 and 27. However, the second and third surfaces 25 and 26 may or may not be parallel. In accordance with Snell's law, the transmitted beam 15 as it emerges from the sheets 12 and 13 will be parallel to the incident beam and offset therefrom by an amount determined by the thickness and index of refraction of the glass. Also, as is well known, when the beam 15 passes through the sheets a portion will be reflected at each surface. Likewise the reflected beams will again be reflected when they strike the next surface. As is illustrated and as can be demonstrated by the laws of optics, beams hich are reflected from parallel surfaces will exit the glass parallel to the transmitted main beam. Thus, those beams reflected from the fourth to the third and from the second to the first surfaces, one of which is shown generally at 28, will be re-reflected to exit the glass parallel to the transmitted main beam 15. However, the beam 29 reflected from the third surface 26 to the second surface 25, where those surfaces are not parallel, will be deviated at an angle twice the angular difference between the plates.

As shown in FIG. 1, the transmitted beam 15 will thus strike the target 15 at the point X and appear as a bright spot thereon, with any parallel beams 28 clustered closely therearound. The deviated beam 29 will strike the target at the point Y. The distance of displacement of the point Y from the point X will indicate the degree of wedge between the second and third surfaces, while the direction of displacement will indicate the direction in which they are off parallel. In paired sheets of glass which are to be laminated, it is thus possible to not only detect areas in which the curvature of the two sheets does not match, but also to detect the degree of slope between the number two and three surfaces and, from that information, determine the amount of stress which would be created in the glass by laminating the sheets together. By providing on the target 17 an indicia such as a circle or an ellipse 30 indicative of the limits of permissible deviation corresponding to acceptable stress in the laminated glass, it is thus possible to quickly and accurately inspect nested pairs of sheets to ascertain their degree of match. In doing so, the mobile base carrying the sheets may be moved to provide for inspection of several areas of the sheets. Obviously, a plurality of light sources and targets may also be positioned to simultaneously observe several points distributed over the sheets.

Figure 3:
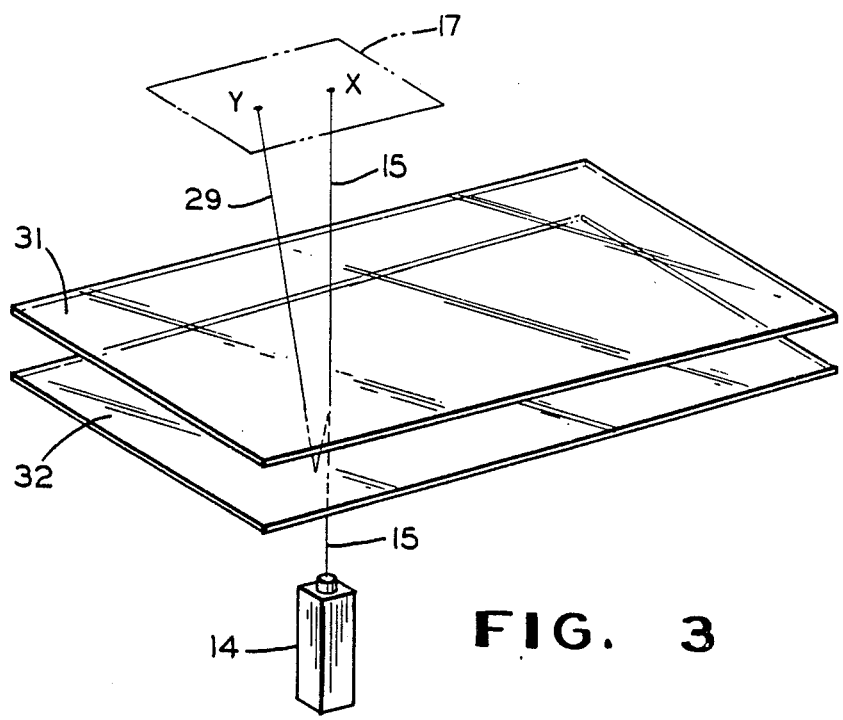
FIG. 3 is a schematic view of an alternate embodiment of the invention.

In accordance with the embodiment of FIG. 3, the invention may be employed to determine when two spaced pieces 31 and 32 of transparent material are parallel to one another as in the manufacture or inspection of insulating glass units. In producing such units, the sheets are supported in spaced relation within the inspection station and their angular relationship is manipulated until the transmitted beam 15 and the deviated beam 29 merge, that is, until the points X and Y on the target 17 coincide. Of course, the device can be used as well for inspecting completed units to determine whether they meet quality standards.

Figure 4:
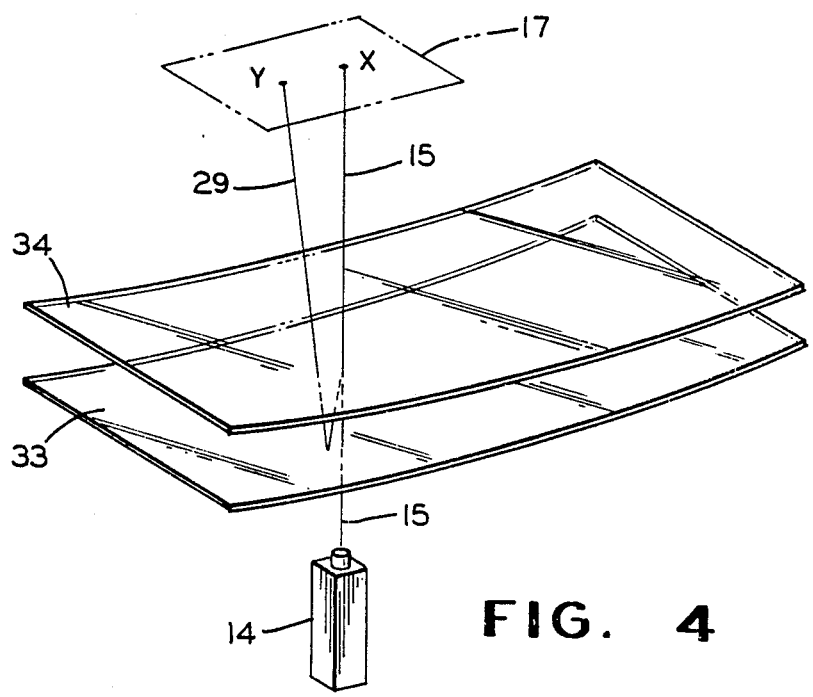
FIG. 4 is a schematic view of another alternate embodiment of the invention.

In the embodiment of FIG. 4 the invention is similarly employed in comparing glazing units to a standard unit having the desired shape. Thus, a "standard" sheet 33 known to have the desired shape is supported as on the mobile base 11, and a sheet 34 whose shape is to be compared to the standard is placed thereon. While the sheet 34 may be placed directly on the sheet 33 as in checking matched pairs for laminating, it is preferred to support them in slightly spaced relation. A deviated beam 29 striking the target at point Y will then visually indicate the amount by which the sample being checked differs from the standard unit. Of course, the positions of the sheets 33 and 34 can be reversed. Likewise the invention can be readily adapted to checking vertically oriented transparent sheets as well as those which are horizontal.

It is contemplated that the invention might be automated as by providing a series of laser beams or scanning beams aimed at photocell quadrant detectors or other beam spacing measuring devices to measure both the direction and magnitude of the misalignment of the two transparent sheets. This data may then be transmitted to an appropriately programmed computer for analysis and classification of the pairs of sheets. As will be readily appreciated, when the slope at various points between the sheets to be laminated is known, the stress induced by subsequently bending the glass to laminate it can be calculated. Thus, from data acquired prior to laminating it is possible to predict the stress which would be present in the laminated unit and to consequently reject such sheets before lamination is completed.

It is to be understood that the forms of the invention herewith shown and described are to be taken as illustrative embodiments only of the same, and that various changes in the shape, size and arrangement of parts, as well as various procedural changes, may be resorted to without departing from the spirit of the invention.

What is claimed is:

1. A method of inspecting paired first and second sheets of transparent material whose surfaces are essentially parallel for determining the wedge angle between the sheets at a selected location, comprising supporting said first and second sheets with one of the major surfaces of each sheet facing one another whereby said one major surface of each said sheet comprises an inner surface, directing a light beam toward said first one of said paired sheets with a major portion of said light beam being transmitted through said first and second sheets and a minor portion of said beam being reflected from said inner surface of said second sheet to said inner surface of said first sheet and then back through said second sheet, intercepting said transmitted beam and said reflected beam after they emerge from said second sheet, and determining the slope and direction between the sheets at the point of inspection from the position of the intercepted reflected beam relative to the position of the intercepted main beam.

2. A method of inspecting paired first and second sheets of transparent material as claimed in claim 1, wherein said second sheet is supported upon said first sheet in nested relationship therewith.

3. A method of inspecting paired first and second sheets of transparent material as claimed in claim 2, wherein said first sheet is supported around its peripheral margin.

4. A method of inspecting paired first and second sheets of transparent material as claimed in claim 1, including the step of moving said sheets and said light beam relative to one another to direct said beam through said sheets at a plurality of selected locations for determining the slope and direction between said sheets at said selected points.

5. A method of inspecting paired first and second sheets of transparent materials as claimed in claim 1, including the step of interposing a target in the path of said transmitted and reflected beams to intercept said beams whereby said transmitted beam creates an image on said target and said reflected beam creates a less intense image on said target, and visually observing the relative positions of the two images for determining the slope and direction between said sheets at said location.

6. A method of inspecting paired first and second sheets of transparent materials as claimed in claim 5, including providing a visible indicia on said target representing a predetermined distance between said two images indicative of an acceptable spacing between said sheets.

7. A method of inspecting paired first and second sheets of transparent materials as claimed in claim 1, including directing a said light beam toward said first one of said paired sheets at a plurality of selected locations for determining the slope and direction between the sheets of each said location.

8. A method of inspecting paired first and second sheets of transparent materials as claimed in claim 1, wherein said light beam is directed toward said first sheet substantially normal to the surface thereof.

9. A method of inspecting paired first and second sheets of transparent materials as claimed in claim 1, wherein said second sheet is supported closely spaced from said first sheet.

10. A method of inspecting paired first and second sheets of transparent materials as claimed in claim 9, including the step of adjusting the angular position of said second sheet relative to said first sheet to cause the position of said intercepted reflected beam to substantially coincide with the position of said intercepted main beam whereby said first and second sheets are parallel.

11. A method of inspecting paired first and second sheets of transparent materials as claimed in claim 9, wherein said first and second sheets are supported around their peripheral margins, and one of said sheets has a predetermined desired configuration.

12. Apparatus for inspecting paired first and second sheets of transparent material whose major surfaces are essentially parallel, comprising a base for supporting said first and second sheets such that one of the major surfaces of each sheet face one another, whereby, said one major surface of each said sheet comprises an inner surface, a light source for directing a light beam toward said first one of said paired sheets whereby a major portion of said beam is transmitted through said first and second sheets and a minor portion of said beam is reflected from said the inner surface of said second sheet to the inner surface of said first sheet and then back through said second sheet, and means positioned opposite said first and second sheets from said light source for receiving said transmitted beam and said reflected beam after they emerge from said second sheet for indicating the slope and direction between the sheets at the point of inspection.

13. Apparatus for inspecting paired sheets of transparent material as claimed in claim 12, wherein said base includes a peripheral frame for supporting said first sheet around its peripheral margin.

14. Apparatus for inspecting paired sheets of transparent material as claimed in claim 13, wherein said second sheet rests upon said first sheet in nested relationship therewith.

15. Apparatus for inspecting paired sheets of transparent material as claimed in claim 13, including peripheral spacer means between said first and second sheets supporting said second sheet spaced from said first sheet.

16. Apparatus for inspecting paired sheets of transparent material as claimed in claim 12, wherein said means for receiving said transmitted and reflected beams comprises a target upon which the beams impinge to produce visible indicia whereby the position of impingement of said reflected beam relative to that of said transmitted beam indicates the slope and direction between the sheets at the point of inspection.

17. Apparatus for inspecting paired sheets of transparent material as claimed in claim 12, wherein said means for receiving said transmitted and reflected beams comprises a photocell quadrant detector.

18. Apparatus for inspecting paired sheets of transparent material as claimed in claim 12, wherein said light source comprises a helium-neon laser unit directing a beam substantially normal to said first sheet.

19. Apparatus for inspecting paired sheets of transparent material as claimed in claim 18, including a plurality of said laser units positioned to direct beams toward said first sheet at of selected locations and means for receiving said transmitted and reflected beams from each said laser unit.

20. Apparatus for inspecting paired sheets of transparent material as claimed in claim 12, including means permitting said base to be moved relative to said light source for directing said light beam toward said first sheet at of a plurality of selected locations thereon.

21. Apparatus for inspecting paired sheets of transparent material as claimed in claim 12, including a mirror positioned opposite said first and second sheets from said light source for deflecting said transmitted and reflected beams to said receiving means.

22. Apparatus for inspecting paired sheets of transparent material as claimed in claim 16, including an indicia on said target defining the amount of deviation of said reflected beam from said transmitted beam representing an acceptable amount of slope between said first and second sheets at the point of inspection.

* * * * *